United States Patent [19]

Roth

[11] 3,953,182

[45] Apr. 27, 1976

[54] COLLECTION MEDIUM FOR AIR SAMPLER

[76] Inventor: Thomas P. Roth, 5025 Hillsboro Road, Apt. 9E, Nashville, Tenn. 32715

[22] Filed: Sept. 3, 1974

[21] Appl. No.: 502,732

[52] U.S. Cl. .................. 55/270; 55/446; 55/485; 55/487; 55/501; 55/502; 55/503; 73/28
[51] Int. Cl.² .......................................... B01D 53/30
[58] Field of Search .................. 55/270, 485–489, 55/501, 502, 465, 511–514, 446, 503; 73/28, 421.5 R; 210/489, 492

[56] References Cited
UNITED STATES PATENTS

| | | | |
|---|---|---|---|
| 155,687 | 10/1874 | Upperman | 55/446 X |
| 1,125,966 | 1/1915 | Combemale | 55/485 X |
| 1,262,317 | 4/1918 | Finney et al. | 210/489 X |
| 1,752,260 | 3/1930 | Calder et al. | 55/446 |
| 2,789,663 | 4/1957 | Camp | 55/513 |
| 3,555,787 | 1/1971 | Lustig | 55/502 UX |
| 3,693,457 | 9/1972 | Pilat | 55/270 UX |
| 3,795,135 | 3/1974 | Andersen | 73/28 |

FOREIGN PATENTS OR APPLICATIONS

| 252,273 | 3/1927 | Italy | 55/446 |
|---|---|---|---|

OTHER PUBLICATIONS
Holland, W. D. and R. E. Conway, "Three Multi-Stage Stack Samplers," *Chemical Eng. Progress,* 69(6): pp. 93–95, June 1973.

*Primary Examiner*—Frank W. Lutter
*Assistant Examiner*—Kathleen J. Prunner
*Attorney, Agent, or Firm*—B. J. Powell

[57] ABSTRACT

A sampling device for separating particles entrained in a gaseous medium including a plurality of plates spaced from each other a prescribed distance with each of the plates defining a plurality of jet impaction apertures therethrough with the apertures of each plate staggered with respect to the apertures of the plates adjacent thereto so that the entrained particles will be separated by jet impaction by each plate on the next downstream plate, a collection substrate carried by the upstream side of each of the plates onto which the particles are impacted and defining a plurality of slots therethrough adapted to overlie the apertures through the plates on which the collection member is carried with means for maintaining a prescribed spacing between the collection substrate and the adjacent upstream plate and for dividing the flow of the gaseous medium through the plates into sub-flow paths.

6 Claims, 6 Drawing Figures

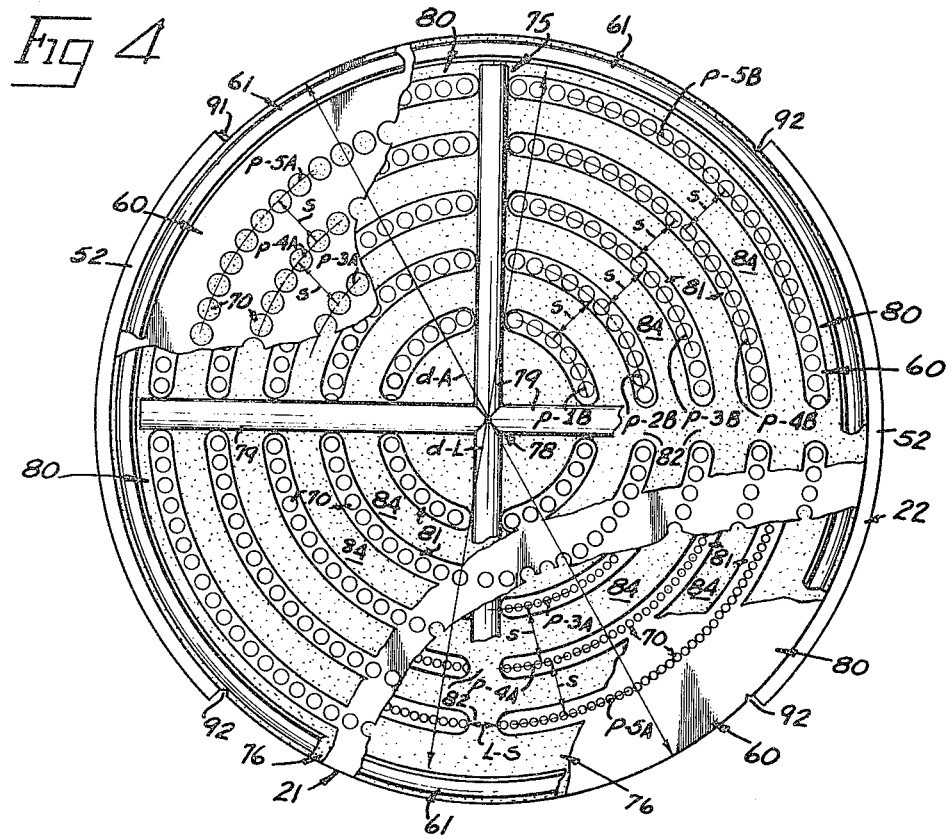
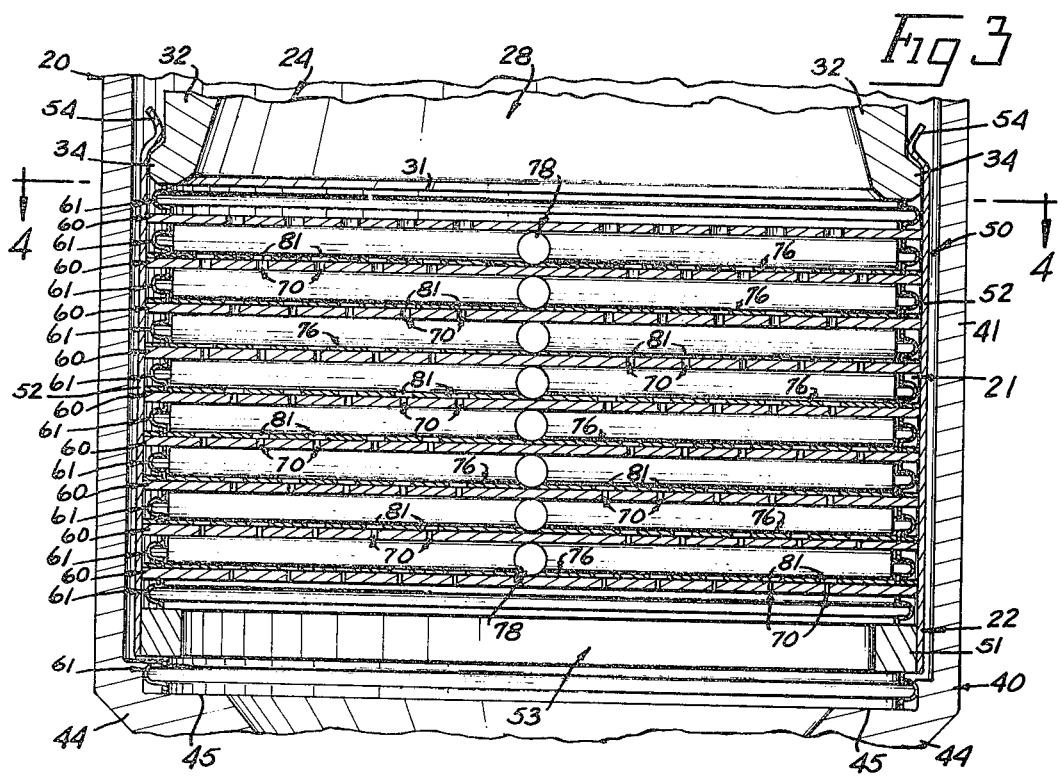

COLLECTION MEDIUM FOR AIR SAMPLER

BACKGROUND OF THE INVENTION

Several types of sampling devices which separate entrained particles from a gaseous medium according to size are available on the market today. Such devices are capable of separating microscopic size particles according to mean particle diameter on the various stages of the device. Examples of such devices are illustrated in U.S. Pat. Nos. 3,693,457 and 3,795,135. One of the problems with such sampling devices, however, is that there is a tendency to re-entrain the particles collected so that the sample is not truly representative of the particles within the gaseous medium. Further, difficulties have been encountered with the use of such sampling devices in that the flow distribution of such devices tended to be unevenly spaced about each stage. Another problem with these devices is that the weighing operation used to quantify the sample collected is difficult.

SUMMARY OF THE INVENTION

These and other problems and disadvantages associated with the prior art are overcome by the invention disclosed herein in that a collection substrate is provided which reduces the tendency toward reentrainment of the particle once it is separated in each stage. Further, means are provided for evenly distributing the flow of the gaseous medium through the device. Further, the collection substrate does not interfere with the overall operation of the device and the collection substrate may be removed and replaced without disabling the device during quantitative analysis of the particles collected. Also, the weighing operation used to quantify the collected particles is simplified.

The apparatus of the invention comprises generally a collection substrate assembly which is interposed between each of the stages of the sampling device. The collection substrate assembly includes a collection substrate having a collection surface thereon which allows the particles to be impacted thereinto to prevent reentrainment of the particles into the gaseous medium. A locater is further provided which cooperates with the collection substrate to insure adequate spacing for the operation of the sampling device while at the same time dividing the flow of the gaseous medium through the sampling device into subparts so that the flow of the gaseous medium through the device is evenly distributed.

These and other features and advantages of the invention disclosed herein will become more apparent upon consideration of the following specification and accompanying drawings wherein like characters of reference designate corresponding parts throughout the several views and in which:

BRIEF DESCRIPTION OF THE DRAWINGS

FIG. 3 is a further enlarged partial longitudinal cross-sectional view of the device of FIGS. 1 and 2;

FIG. 4 is a cross-sectional view taken along line 4—4 in FIG. 3 and partially broken away to show the construction thereof;

These figures and the following detailed description disclose specific embodiments of the invention, however, it is to be understood that the inventive concept is not limited thereto since it may be embodied in other forms.

DETAILED DESCRIPTION OF ILLUSTRATIVE EMBODIMENTS

Figures 1, 2:
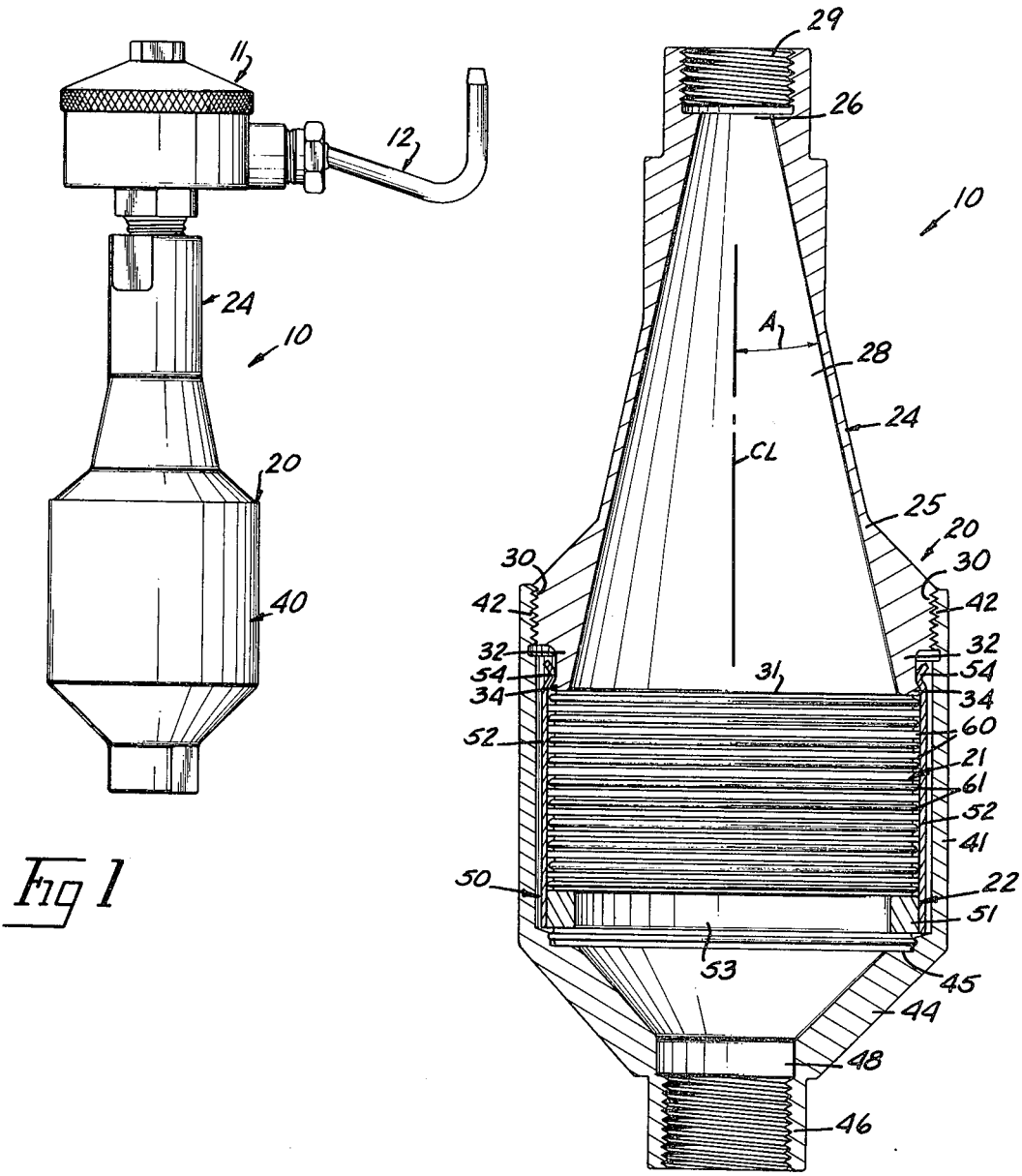
FIG. 1 is a side elevational view of a sampling device embodying the present invention.
FIG. 2 is an enlarged longitudinal cross-sectional view of the device of FIG. 1.

Referring to the figures, it will be seen that the invention is embodied in an air sampling device 10 in which particles entrained in a gaseous medium are separated according to the mean diameter of the particle. The sampling device 10 is illustrated in FIG. 1 with a preseparating device 11 mounted upstream of device 10 on the inlet thereof for preseparation of particles having a mean diameter above the operating range of the sampling device 10. Such a preseparating device is illustrated in my co-pending application Ser. No. 502,344 filed on the same day as this application. The preseparator unit 11 has a pick-up nozzle 12 which is disposed in the gaseous medium to be sampled and its outlet is connected to the inlet of the sampling device 10. It will further be noted that the sampling device 10 is especially designed for the sampling of high temperature gases in the temperature range up to 1500°F.

Referring to FIG. 2, it will be seen that sampling device 10 includes a case 20 and a jet plate assembly 21 carried within the case 20 by a plate holder 22. The case 20 comprises an inlet tube 24 having an annular side wall 25 concentrically about the centerline CL of the sampling device 10. The inlet tube 24 has an inlet port 26 and wall 25 defines a diverging passage 28 therethrough communicating with inlet port 26. The inlet tube 24 is internally threaded as indicated at 29 at the inlet port 26 to mount the preseparator unit 11 thereon and is externally threaded as indicated at 30 at its downstream end for connection to the rest of the case 20 as will be explained. It will further be noted that the downstream end 31 of the inelt tube 24 is oriented substantially normal to the centerline CL and the side wall 25 is provided with a recessed lip 32 having a bead 34 on the downstream end thereof to mount the plate holder 22 thereon as will become more apparent. It will further be noted that the passage 28 defines an included angle A with respect to the centerline CL. The case 20 further includes a tubular body 40 attached to the downstream end of the inlet tube 24 and includes an annular cylindrical side wall 41 which is internally threaded as indicated at 42 at its upper end to be screwed onto the threads 30 on the lower end of the inlet tube 24. The downstream end of side wall 41 is provided with an annular inwardly tapering conical wall 44 which has a thickness greater than the side wall 41 so as to provide a shoulder 45 at the juncture of the side wall 41 with the conical wall 44. The downstream end of the conical wall 44 is provided with a boss 46 defining an outlet passage 48 therethrough which is internally threaded for connection to a vacuum source to power the sampling device 10. Thus, it will be noted that a sampling chamber 50 is provided within the body 40 downstream of the end 31 of inlet tube 24 as best seen in FIG. 2. The jet plate assembly 21 and plate holder 22 are carried within this chamber 50 as will become more apparent.

Referring now to FIGS. 3 and 4, it will be seen that the plate holder 22 comprises generally an annular support ring 51 defining the central opening 53 therethrough. A pair of opposed upstream extending side plates 52 are attached on oppsite outside edges of the ring 51 and they have an inside diameter corresponding to the outside diameter of the ring 51. Each of the side plates 52 has detents 54 at the upstream end thereof which is adapted to snap over the bead 34 on the downstream end of the inlet tube 24 to hold the plate holder 22 in position during assembly of the case 20. The jet plate assembly 21 is retained between the side plates 52 and supported on the ring 51 so that the detent 54 can be snapped over the bead 34 on inlet tube 24 to hold the jet plate assembly 21 in position on the downstream end 31 of the inlet tube 24 during assembly.

The jet plate assembly 21 comprises a plurality of jet plates 60 spaced apart by a plurality of sealing rings 61. Each of the jet plates 60 has a diameter $d$-A substantially equal to the inside diameter of side plates 52 so that plates 60 can be stacked within the holder 22 on support ring 51 between side plates 52. One of the sealing rings 61 is positioned above and below each plate 60 so that the plates 60 are supported in a spaced apart condition with the plane of each plate 60 substantially normal to the centerline CL and concentric therewith. Because each plate 60 has a different jet passage configuration, the plates have been individually labeled 60-0 through 60-8 that corresponds to each of the separation stages as will become more apparent.

Figure 5:
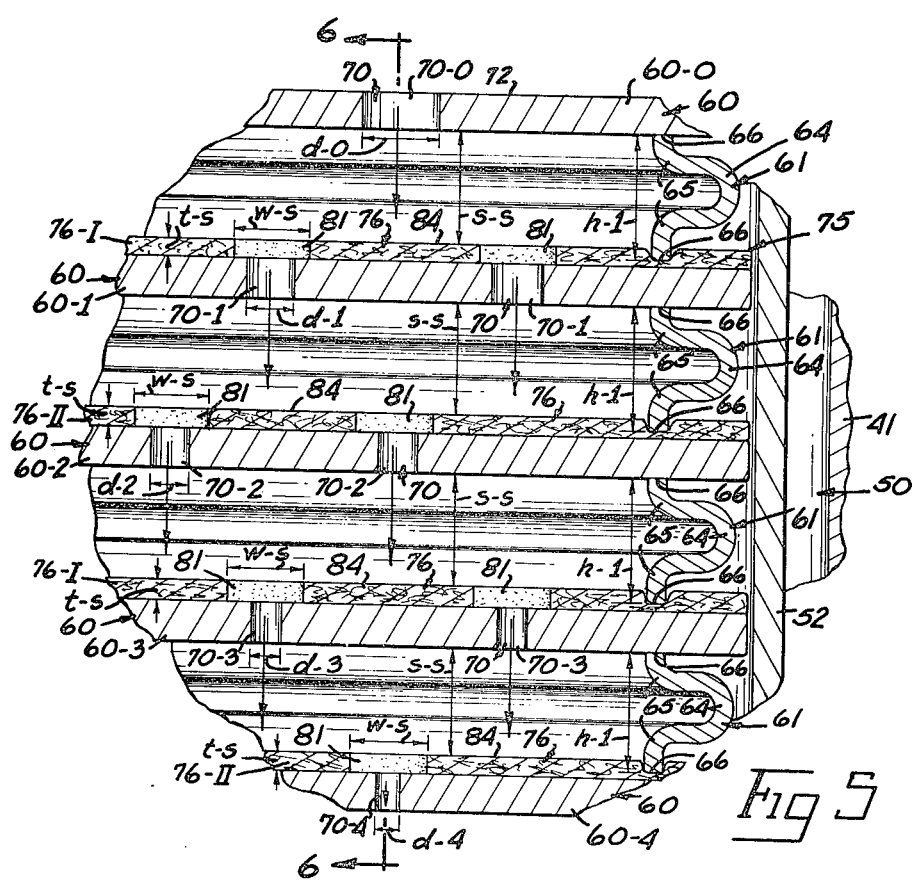
FIG. 5 is a further enlarged partial longitudinal cross-sectional view similar to FIG. 3 showing the operation of the device; and, FIG. 6 is a cross-sectional view taken along line 6—6 in FIG. 5.

Each of the sealing rings 61 as best seen in FIG. 5 has a cross-sectional shape with a curved central section 64 integral with opposed sealing flanges 65 along opposite inside edges thereof. Each of the sealing flanges 65 defines a sealing face 66 which is arranged substantially normal to the centerline CL. The faces 66 are spaced apart a height $h$-1 that determines the spacing between plates 60. It will also be noted that the major outside diameter of rings 61 is substantially equal to diameter $d$-A.

Figure 6:
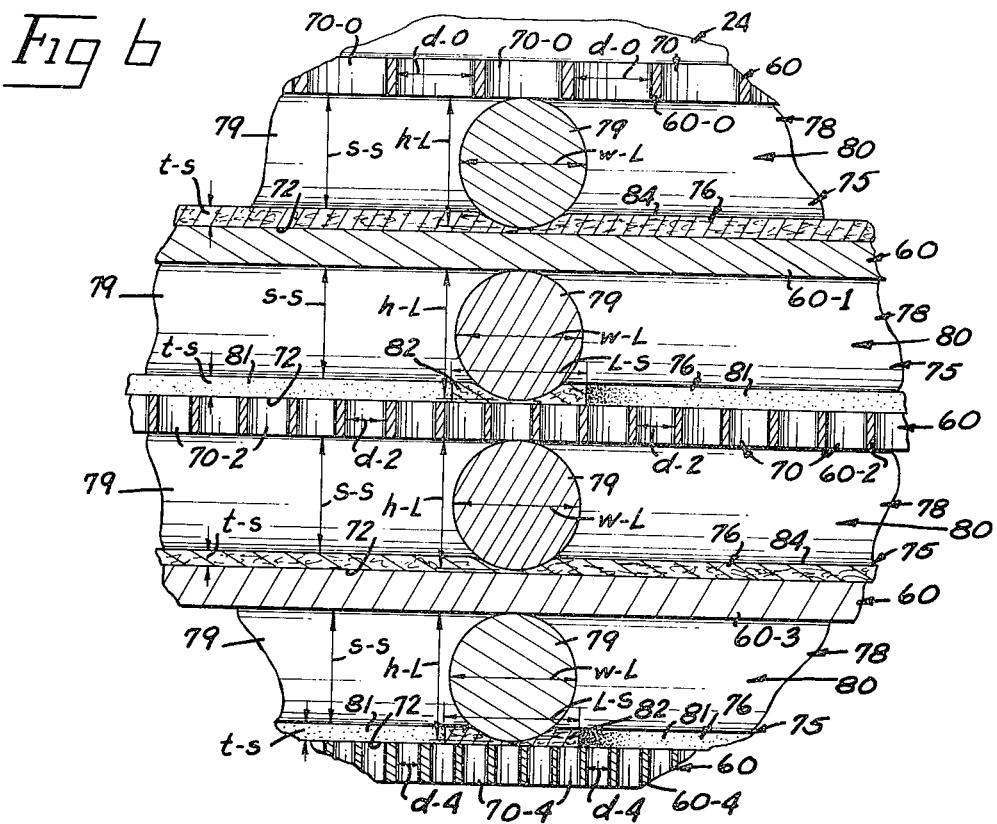

Referring to FIGS. 3, 5 and 6, it will be noted that each plate 60 has a plurality of jet impaction apertures 70 therethrough oriented generally parallel to the centerline CL. Because the diameters of these apertures vary from plate to plate, they have been individually referenced 70-0 through 70-8 similarly to plates 60. The apertures 70 are arranged along five circular paths $p$-1A through $p$-5A in plate 60-0, 60-2, 60-4, 60-6 and 60-8 concentrically about centerline CL. The apertures 70 are arranged along five circular paths $p$-1B through $p$-5B in plates 60-1, 60-3, 60-5 and 60-7. It will be noted that a space s is provided between paths $p$-1A through $p$-5A and between paths $p$-1B through $p$-5B but paths $p$-1B through $p$-5B are staggered with respect to paths $p$-1A through $p$-5A so that the jet impaction passages 70 in any plate 60 cause the gaseous medium to impinge on the upstream surface 72 of the adjacent downstream plate 60 between the apertures 70 through the adjacent downstream plate as best illustrated in FIG. 5.

Because the velocity of the gaseous medium determines which particles will be deposited on the plate below each aperture 70 and because the total volume of gaseous medium passing through the sampling device is relatively fixed, the particular velocity through an aperture 70 is determined by the diameter of aperture 70. Thus, the mean diameter of the particles collected by stage is determined by the diameter of the aperture 70.

The diameter of the apertures 70 decreases as one moves downstream through the sampling device 10 with the largest diameters in plate 60-0 and the smallest in plate 60-8. Thus, the apertures 70-0 have diameter $d$-0, apertures 70-1 have diameter $d$-1, apertures 70-2 have diameter $d$-2, et. seq. It will be seen that the largest particles will be separated by apertures 70-0 onto the upstream surface 72 of plate 60-1 and the smallest particles will be separated by apertures 70-7 onto the upstream surface 72 of plate 60-8.

A collection substrate assembly 75 is mounted on the upstream surface 72 of each of plates 60-1 through 60-8 as seen in FIGS. 3–6. Each collection substrate assembly 75 comprises a collection substrate 76 having a diameter substantially diameter $d$-A so that it will fit between the side plates 52 of holder 22 and a thickness $t$-s as will become more apparent. The substrate 76 is held in place about is periphery by one of the sealing faces 66 of the sealing ring 65 and across its cross-section by a locator-divider 78 which fits within the sealing ring 61 upstream of the substrate 76. Each locator-divider 78 also serves to subdivide the flow of gaseous medium through the device 10 as will become more apparent.

The locator-divider 78 comprises a pair of cross bars 79 joined at their centers so that they lie in a common plane. The locator-divider has an effective diameter $d$-L substantially equal to the inside diameter of sealing rings 61 and a height $h$-L as will become more apparent. Each of the cross bars 79 have a prescribed width $w$-L approximately equal to height $h$-L so that open quadrants 80 are defined between cross bars 79 as will become more apparent.

Each of the substrates 76 define a plurality of arcuate slots 81 therethrough which are aligned with the jet impaction apertures 70 of the plate 60 carrying the substrate. Because the configuration of slots 81 corresponds to that of the apertures 70, the substrates 76 have a first configuration designated 76-I for use with plates 60-1, 60-3, 60-5 and 60-7; and a second configuration designated 76-II for use with plates 60-2, 60-4, 60-6 and 60-8. For substrate 76-I, the slots 81 are arranged along and centered on paths $p$-1B through $p$-5B whereas for substrate 76-II, the slots 81 are arranged along and centered on paths $p$-1A through $p$-5A. Thus, the apertures 70 are centered under slots 81. It will also be noted that the slots 81 are interrupted by radially extending lands 82 arranged to underlie the cross bars 79. Four lands 82 are illustrated since the cross bars 79 divide the space between plates 60 into quadrants and extend between the slots 81 on each path. The slots 81 have a prescribed width $w$-s which is larger than the largest diameter aperture 70 with which it is to be used. It will further be noted that the lands 82 have a width L-S which is wider than the width W-L of cross bars 79 so that those apertures 70 which underlie the cross bars 79 will be blocked to prevent inaccurate collection. An arcuate collection surface 84 is defined by substrate 76 between adjacent slots 81 that is centered under the apertures 70 of the next upstream plate 60 so that the gaseous medium will impinge thereon to deposit the particles of a particular mean diameter onto the surfaces 84 as seen in FIG. 5.

The particles collected may have a sticky coating such as a petroleum product or be dry depending on the particular gaseous medium being sampled. Where the particles are dry, they are especially hard to collect since they do not adhere well to a smooth surface and also tend to bounce upon impaction. Both of these conditions promote undesirable reentrainment of the particles in the gaseous medium to give inaccurate collection. The substrates 76 solve this problem where the material of the substrate is selected so that it entraps the particles. One material that successfully entraps these particles is glass fiber such as that designated Type A. The thickness $t$-$s$ is selected so that the gaseous medium does not flow therethrough to any appreciable extend and is very small when compared with the spacing between plates 60 so that the flow pattern of the gaseous medium through the device 10 is not significantly disturbed. Because the upstream surface 72 of each plate 60 underlies the collection surfaces 84 to block the flow of the gaseous medium therethrough, the thinness of the substrate 76 causes virtually none of the gaseous medium to pass through the substrate to disturb its flow pattern. While different thicknesses $t$-$s$ may be used, it has been found that a thickness $t$-$s$ of 0.010–0.015 inch or about 10–15 percent of space $s$-$s$ performs as set forth above when glass fiber is used.

Where the particles to be collected are sticky so that they will adhere to smooth surface, the substrates 76 may be made out of a metal foil such as aluminum or stainless steel. Because the weight of the substrates 76 is much less than the weight of the plates 60, the weighing process used to quantify the collected particles is greatly simplified.

The width $w$-$s$ of slots 81 is greater than the diameter of the apertures 70 through plates 60 which underlie the slots 81. This insures that the flow pattern through the apertures 70 will not be significantly affected by the substrate 76 due to increased wall losses or greater passage length. While different widths $w$-$s$ may be used, it has been found that a width $w$-$s$ which is at least 25 percent greater than the diameter of the apertures 70 which underlies the slots 81 performs satisfactory.

The height $h$-L of each locator-divider 78 is less than the height $h$-1 of the sealing rings 61 so that the sealing rings seal the peripheral edges of each substrate 76 when the jet plate assembly 21 is clamped together and space the plates 60 apart the distance equal to space $s$-$s$ plus the thickness $t$-$s$ as seen in FIGS. 5 and 6. The height $h$-L of each locator-divider 78 is, however, greater than the space $s$-$s$ between the upstream surface 84 of substrate 76 and the downstream surface of the next upstream plate 60 so that the locator-divider 78 is forced against the lands 82 of substrate 76 to seal the substrate 76 against the upstream surface 72 of the underlying plate 60. This action serves two functions. The first is to keep the substrate 76 lying against the upstream surface 72 of the underlying jet plate 60. The second is to divide the flow of the gaseous medium through the plates 60 into quadrants to evenly distribute the flow therethrough.

It will further be noted that the lands 82 of substrates 76 and locator-dividers 78 are longitudinally aligned through the device 10 to produce accurate readings. To assist in locating the relative rotational positions of the plates 60, pins 91 may be provided in the periphery of the most upstream plate 60-1, one of which is seen in FIG. 4, that fit on opposite sides of the side plates 52 to positively locate plate 60-1. Notches 92 may be provided in the rest of plates 60 to allow them to be visually oriented during assembly. The notches 92 allow expansion and contraction of the plates 52 without binding.

It is to be understood that full use may be made of modifications, substitutions and equivalents without departing from the scope of the invention as disclosed herein.

I claim:

1. A sampling device comprising a casing having an upstream inlet and a downstream outlet for separating particles entrained in a gaseous medium from the gaseous medium as the gaseous medium with the particles entrained therein passes through the sampling device from its upstream end to its downstream end, said sampling device comprising:

a plate holer having a centerline and disposed between said upstream inlet and downstream outlet;

a jet plate assembly having an upstream end and a downstream end through which a gaseous medium with particles entrained therein passes, said jet plate assembly including a plurality of jet plates carried by said plate holder so that said jet plates are serially aligned on said centerline parallel to each other, each of said jet plates oriented generally normal to said centerline, said jet plates including a first jet plate at the upstream end of said jet plate assembly and a plurality of second jet plates downstream of said first jet plate, each of said jet plates defining an upstream surface and a downstream surface thereon generally parallel to each other and normal to said centerline, each of said jet plates defining a plurality of jet impaction passages therethrough arranged along paths concentric about said centerline, each of said jet impaction passages oriented generally parallel to said centerline and opening onto said upstream surface and said downstream surface of each of said jet plates, said jet impaction passages in each of said jet plates located different distances from said centerline than said jet impaction passages in said jet plate adjacent to and immediately upstream of each of said jet plates so that said jet passages in each of said jet plates are staggered with respect to the adjacent downstream jet plate and the gaseous medium passing through said jet impaction passages of each of said jet plates is directed toward said upstream surface between said jet impaction passages of the adjacent downstream jet plate, each of said jet plates having an outer periphery outboard of said jet impaction passages therethrough;

a plurality of resilient collection substrates, each of said substrates having a first prescribed thickness, one of said substrates carried by and in juxtaposition with said upstream surface of each of said second jet plates, each of said collection substrates defining a plurality of arcuate slots therethrough arranged along slot paths concentric about said centerline, each of said slots overlying a plurality of said jet impaction passages opening onto said upstream surface of each of said second jet plates carrying said collection substrate, each of said slots having opposed ends and a plurality of slots lying along each concentric slot path, said substrate defining a land between the ends of adjacent slots lying along the same slot path, said lands in each of said slot paths radially aligned with one of said lands in each of the other of said slot paths of said substrate, said substrate further defining an arcuate collection surface between said arcuate slots facing the adjacent upstream jet plate so that the gaseous medium passing through said jet passages of said adjacent upstream jet plate impinges on said collection surface, a plurality of annular sealing rings, one of said sealing rings mounted between each of said collection substrates and the adjacent upstream jet plate outboard of said jet passages and said slots concentrically about said centerline, each of said sealing rings having a first prescribed height;

clamping means operatively associated with said casing for forcing said jet plates toward each other to cause said sealing rings to form a seal about and between the outer periphery of said jet plates and position said jet plates parallel to each other, a space having a second prescribed height greater than said first prescribed thickness of said substrates defined between said collection surfaces of each of said substrates and the adjacent upstream jet plate, said jet plates spaced apart a first prescribed distance greater than said second prescribed height of said space; and a plurality of locator-dividers, one of said locator-dividers positioned between each of said substrates and the adjacent upstream jet plate, and lying within said sealing rings, each of said locator-dividers including a plurality of crossbars, each of said cross bars radially extending from said centerline and having a third prescribed height greater than said second prescribed height of said space and less than said first prescribed distance between said plates, each of said cross bars engaging one of said substrates on said radially aligned lands between the ends of said slots so that said substrate is compressed thereby and the resiliency of said substrate causes said substrate to force said cross bars into sealing engagement with the downstream surface of the next upstream jet plate of said jet plates.

2. The sampling device of claim 1 wherein said jet impaction passages have a fourth prescribed maximum width measured radially with respect to said centerline, wherein said slots have a fifth prescribed minimum width measured radially with respect to said centerline greater than said fourth prescribed maximum width, and wherein said slots are centered over said jet impaction passages.

3. The sampling device of claim 2 wherein said jet impaction passages are circular in cross-section, said fourth prescribed maximum width being the diamter of said passages.

4. The sampling device of claim 3 wherein said jet impaction passages of said first jet plate has a diameter equal to said fourth prescribed maximum width and wherein each of said jet impaction passages of said second jet plates has a diameter less than said fourth prescribed maximum width, the diameters of all of said jet impaction passages through each said second jet plate being substantially equal and the diameters of said jet impaction passages in each said second jet plate being less than the diameters of the jet passages in the adjacent upstream plate.

5. The sampling device of claim 1 wherein each of said lands between adjacent ends of said slots in said collection substrates has a sixth prescribed width measured between the adjacent ends of said slots, and wherein each of said cross bars has a seventh transverse width less than said sixth prescribed width.

6. The sampling device of claim 1 wherein said plate holder includes a pair of opposed generally parallel side plates located on diametrically opposite sides of said centerline and generally parallel thereto, said jet plates removably carried between said side plates, each of said side plates having opposed side edges, said first jet plate including at least one pair of locating pins carried by the periphery of said first jet plate and adapted to fit on said side edges of one of said side plates to fix the relative rotational position of said first jet plate with respect to said side plate, each of said second jet plates defining at least one pair of notches in the periphery thereof aligned with said opposed side edges of one of said side plates to determine the relative rotational position of said second jet plates with respect to said side plate.

* * * * *